United States Patent
Grimm

[11] Patent Number: 5,817,054
[45] Date of Patent: Oct. 6, 1998

[54] VETERINARY IMPLANTER WITH DISINFECTANT DISPENSER

[75] Inventor: C. Louis Grimm, Shawnee, Kans.

[73] Assignee: Ivy Laboratories, Inc., Overland Park, Kans.

[21] Appl. No.: 748,173

[22] Filed: Nov. 12, 1996

[51] Int. Cl.[6] .................................................. A61M 31/00
[52] U.S. Cl. ............................... 604/62; 604/57; 604/61; 604/63; 604/51
[58] Field of Search ................... 604/57, 61, 62, 604/56, 59, 60, 63, 64

[56] References Cited

U.S. PATENT DOCUMENTS

| | | |
|---|---|---|
| 842,631 | 1/1907 | Deperdussin . |
| 1,109,072 | 1/1914 | Kozmousky . |
| 1,248,613 | 12/1917 | Chapman . |
| 1,347,622 | 7/1920 | Deininger . |
| 2,502,909 | 4/1950 | Wick et al. . |
| 2,850,013 | 9/1958 | Cordis . |
| 2,883,984 | 4/1959 | Candido, Jr. et al. . |
| 3,520,299 | 7/1970 | Lott et al. . |
| 3,538,916 | 11/1970 | Wiles et al. . |
| 3,669,104 | 6/1972 | Wyatt et al. . |
| 3,774,607 | 11/1973 | Schmitz . |
| 4,154,239 | 5/1979 | Turley . |
| 4,223,674 | 9/1980 | Fluent et al. . |
| 4,400,170 | 8/1983 | McNaughton et al. . |
| 4,447,223 | 5/1984 | Kaye et al. . |
| 4,518,384 | 5/1985 | Tarello et al. . |
| 4,576,591 | 3/1986 | Kaye et al. . |
| 4,637,819 | 1/1987 | Mann . |
| 4,659,326 | 4/1987 | Johnson et al. . |
| 4,673,387 | 6/1987 | Phillips et al. . |
| 4,687,465 | 8/1987 | Prindle et al. . |
| 4,762,515 | 8/1988 | Grimm . |
| 4,784,640 | 11/1988 | Johnson et al. . |
| 4,787,384 | 11/1988 | Campbell et al. . |
| 4,799,921 | 1/1989 | Johnson et al. . |
| 4,976,686 | 12/1990 | Ball et al. . |
| 5,135,493 | 8/1992 | Peschke . |
| 5,147,295 | 9/1992 | Stewart . |
| 5,370,611 | 12/1994 | Niczink et al. ................ 604/59 X |
| 5,522,797 | 6/1996 | Grimm . |

Primary Examiner—Wynn Wood Coggins
Assistant Examiner—N. Kent Gring
Attorney, Agent, or Firm—Litman, McMahon & Brown, L.L.C.

[57] ABSTRACT

A veterinary implanter includes an attached disinfectant dispenser including a reservoir for holding a quantity of disinfectant, a pump attached to the reservoir, and a special needle holder spray tip with the implanter including a conduit which has an inlet opening connected to the disinfectant pump. An exit opening of the conduit is coupled to the needle spray tip which is designed to spray disinfectant 360 degrees about the inlet end of a hypodermic needle cannula which is held in place against the spray tip by a threaded needle holder extension. The inventive disinfectant dispenser thus allows an operator of the implanter to selectively inject a quantity of disinfectant into the needle with each implant, with the disinfectant then being carried by the implanted pellets into a wound created by the needle.

18 Claims, 2 Drawing Sheets

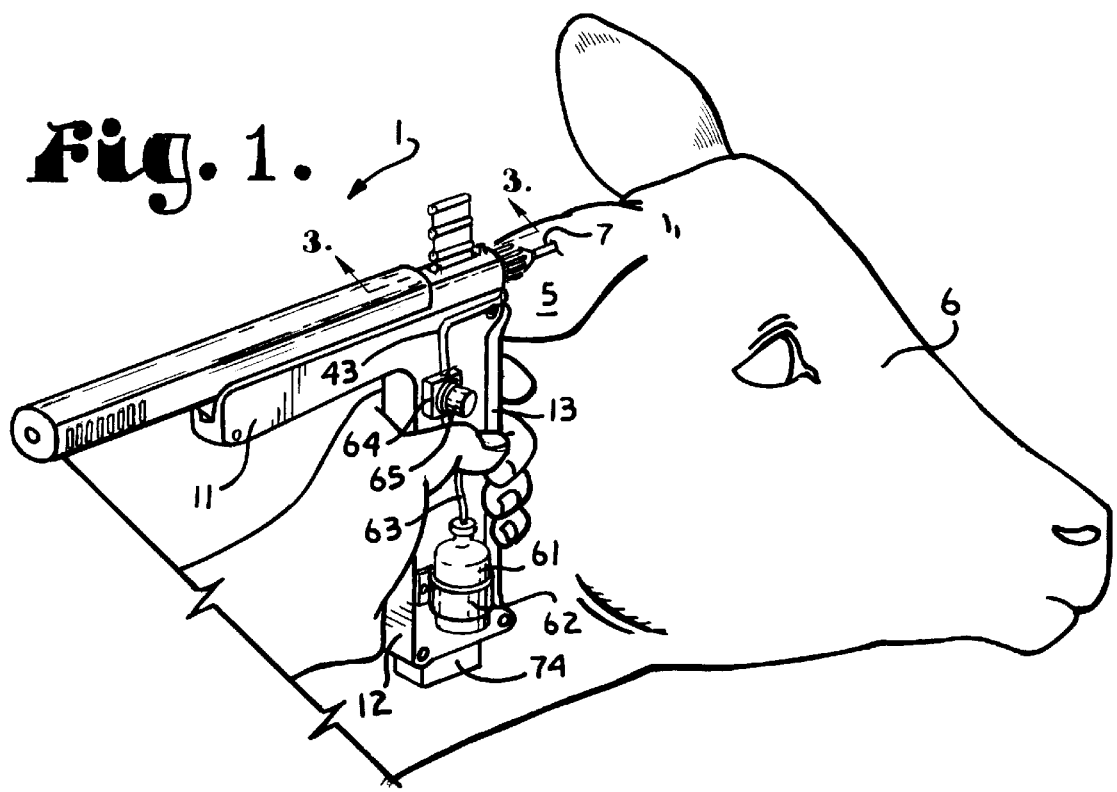
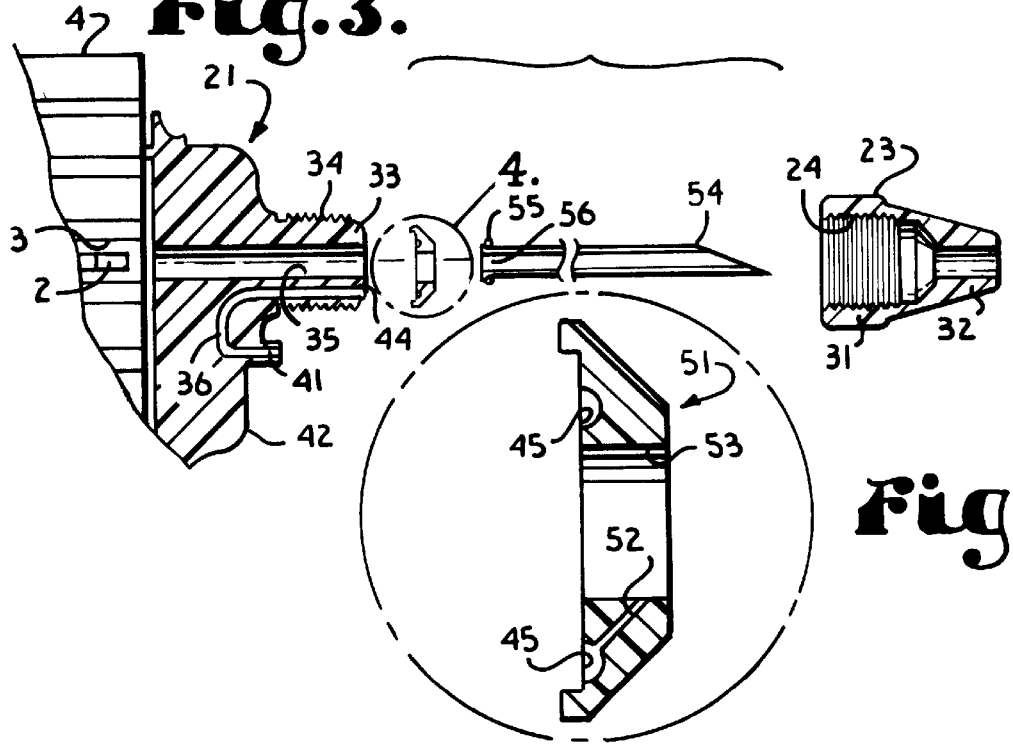

VETERINARY IMPLANTER WITH DISINFECTANT DISPENSER

FIELD OF THE INVENTION

The present invention relates to a veterinary implanter with disinfectant dispenser, and, more particularly, to such an implanter with a disinfectant reservoir and pump with a spray head attached to a hypodermic needle such that selective operation of the pump moves disinfectant from the reservoir to the spray head and into a cannula within the needle.

BACKGROUND OF THE INVENTION

Currently, growth stimulants are used to enhance the body weight of animals which are raised for slaughtering, such as cattle, swine, turkeys, chickens, and the like. In the case of cattle and swine, approved growth hormones are, administered as solid pellets which are injected by an implanter equipped with a hypodermic needle. The needle is used to make a small, non-coring puncture wound into the ear of an animal and small pellets of growth hormone are forced through the needle and left in the ear as the needle is removed from the ear. The ears are commonly discarded in slaughtering, such that no unabsorbed residues of such pellets will end up in food products intended for humans or domestic animals. The pellets are formulated for timed release and absorption of the active ingredients over an extended period of time.

The pellets are normally implanted while an animal is confined in a chute. An ear is grasped in one hand, and an implanter device having a large hypodermic needle is used to puncture the hide to enable a pellet dose to be injected between the hide and the next layer of tissue in the ear. The implanting must be done carefully to insure that the pellets are properly placed and that no pellet remains in the puncture in the hide, which could result in an infection. At the same time, the procedure must be carried out quickly since the animals are not entirely cooperative and may shake their heads to free the held ear. Further complicating the matter is that other procedures may be occurring at the same time as the implanting operation while the animal is confined, such as ear tagging, branding, veterinary inspections or procedures, or the like, which may further excite the animal.

In U.S. Pat. No. 5,522,797 to the present inventor (hereinafter "the '797 patent"), and entitled Slide Action Veterinary Implanter, which patent is hereby incorporated by reference, an implanter employs a slide action mechanism to retract an impeller, store an impeller driving force in a spring in cooperation with a latch mechanism, reset a trigger, and advance a pellet magazine, all by a single reciprocation of the slide mechanism. Operation of the trigger then forces the pellets from the pellet magazine through the needle and into the animal's ear.

With efficient implanters such as that taught in the '797 patent, typically a large number of cattle or swine are implanted in rapid sequence, with the same needle often used with as many as 100 or more animals. Furthermore, these injections often occur in or near feedlots or other locations with considerably less than ideal sanitary conditions. Since these implantations involve the deliberate making of a puncture wound in the animal's ear, bacteria are carried into each animal's ear in varying degrees. This can cause a bacterial infection in the receiving animal, and, depending upon several factors, sometimes a bacteria-induced abscess can occur in the wound area, which can result in a "walling-off" of the implant, thereby reducing the effectiveness of the implant and delaying or preventing the healing of the implant area.

It is clear then, that a need exists for a reliable, effective, inexpensive and convenient apparatus and method of disinfecting the needle of an implanter such as that taught in the '797 patent, as well as introducing a disinfectant into the ear puncture wound forming the implant area of each receiving animal.

SUMMARY OF THE INVENTION

The present invention is directed to a veterinary implanter with disinfectant dispenser. The disinfectant dispenser includes a reservoir for holding a quantity of liquid disinfectant, a pump attached to the reservoir, and a special needle holder spray tip with the implanter including a needle receiver with an internal conduit which has an inlet end connected to a tube leading from the disinfectant pump. An exit end of the conduit has an exit opening connected to the needle spray tip which is designed to spray disinfectant 360 degrees about the inlet end of a cannula of a hypodermic needle which is held in place against the spray tip by a threaded needle holder extension. The inventive disinfectant dispenser thus allows an operator of the implanter to selectively inject a quantity of disinfectant into the needle with each implant, with the disinfectant then being carried by the implanted pellets into the wound created by the needle. In a first embodiment, the reservoir is attached directly to a grip portion of the implanter housing, and, in a second embodiment, a removable pellet magazine drum includes the reservoir and pump positioned within a spiral of pellet magazines.

OBJECTS AND ADVANTAGES OF THE INVENTION

The principal objects of the present invention include: to provide an improved veterinary implanter with disinfectant dispenser; to provide such a device of the type including a large hypodermic needle which is used to puncture the skin or hide of an animal and through which a stack of pellets is moved by an elongated impeller member; to provide such a device which allows an operator to selectively introduce a liquid disinfectant into the needle; to provide such a device in which the disinfectant is sprayed 360 degrees about the inlet end of the needle cannula by a special spray tip; to provide such a device in which the disinfectant in the needle is then carried into the puncture wound by the stack of pellets which are loaded into the needle from a magazine chamber and forced through the needle and into the puncture wound; to provide such a disinfectant dispenser which can be attached to the implanter, or, alternatively, can be carried in a pellet magazine drum attached to a base of the implanter; and to provide such a device which is economical to manufacture, which is positive and efficient in operation, which is effective to disinfect the implanter needle and the puncture wound, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is a perspective view of a veterinary implanter apparatus which includes a first embodiment of the present invention, shown with the implanting needle inserted into an animal's ear.

FIG. 3 is a greatly enlarged, fragmentary, cross sectional exploded view, taken along line 3—3 of FIG. 1, and illustrating the internal details of a spray tip, needle holder with conduit and threaded needle extension usable with both embodiments of the invention.

FIG. 4 is a greatly enlarged cross sectional view of the area of FIG. 3 highlighted by a circle and labeled as "4", illustrating the spray tip in greater detail.

DETAILED DESCRIPTION OF THE INVENTION

Figure 2:
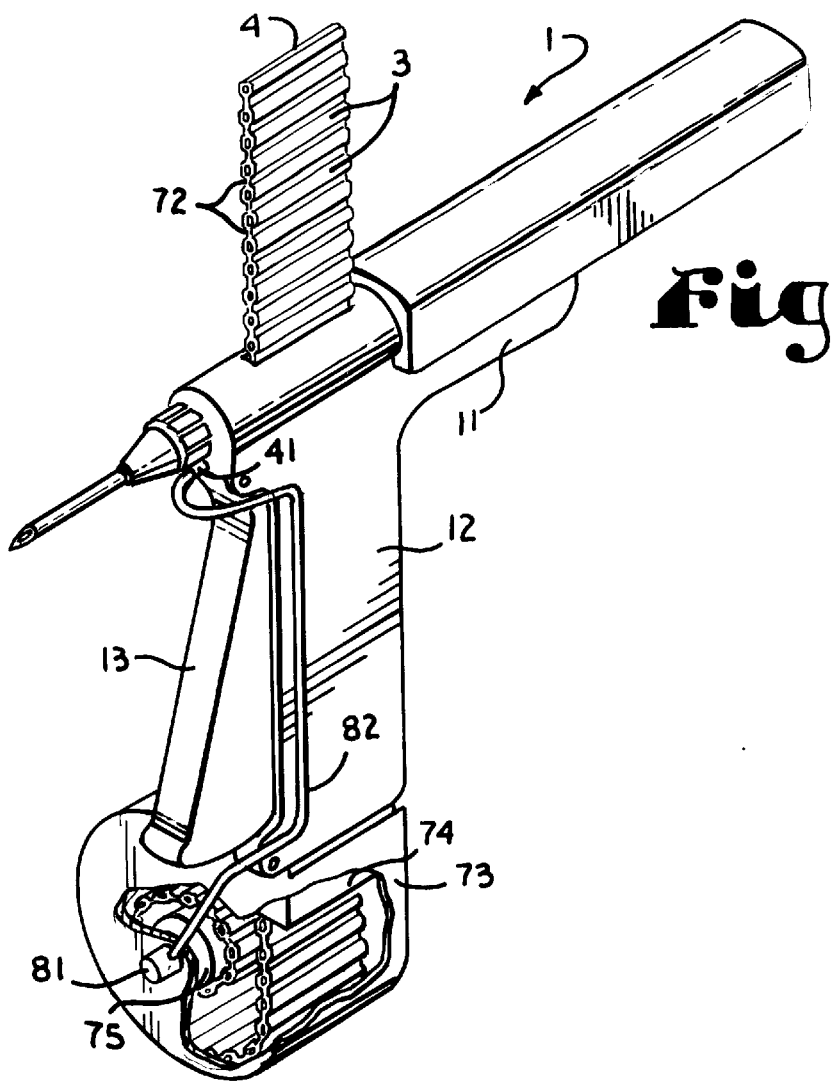
FIG. 2 is a second perspective view of a veterinary implanter apparatus, which implanter includes a second embodiment of the present invention with the disinfectant reservoir and pump contained within a pellet magazine drum which is snapped onto a lower end of the implanter grip housing.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a slide action veterinary implanter apparatus with integral disinfectant dispenser which embodies the present invention. The apparatus 1 is used to implant solid form drugs, such as pellets 2 (FIG. 2) from a pellet chamber 3 of a magazine strip 4 into an ear 5 of an animal 6 through a hypodermic needle 7.

The implanter apparatus 1 is illustrated and described in detail in the '797 patent, and generally includes a housing 11 having a grip portion 12 with a trigger assembly 13 pivotally mounted therein. An impeller assembly 14 (FIG. 5), including an impeller member 15, is slidably mounted within the housing 11 in alignment with the needle 7 and one of the chambers 3 of a loaded pellet magazine strip 4. The needle 7 is used to puncture through the skin or hide of a part of the animal's ear 5, and the trigger assembly 13 is pivoted into the grip portion 12 of the housing 11, causing impeller member 15 to be urged through the magazine chamber 3, thereby forcing a stack of pellets 2 through a cannula 8 of the needle 7 and into a portion of the ear 5.

The needle 7 is attached to the implanter 1 via a needle assembly, generally indicated at 21, which assembly 21 includes a needle holder extension 23 with female threads 24. The needle holder extension 23 is generally cylindrical in shape and is formed by cylindrical walls 31 which terminate in a tapered end section 32. The needle holder extension 23 is adapted to mate with a needle receiver 33 in the implanter housing 11 with the receiver being equipped with mating male threads 34. The needle receiver 33 includes an internal channel 35 which is sized to mate with the interior cylindrical cannula 8 of the needle 7 and at least one conduit 36 is integrally formed within the needle receiver 33 with the conduit 36 including an inlet end 41 opening forward from a front wall 42 of the needle receiver 33 such that the inlet end 41 is connectable with a flexible hose 43. The conduit 36 also has an exit outlet 44 which opens outward from the needle receiver 33 into a concentric channel 45 formed in a spray tip 51. The concentric channel 45 opens into one or more disinfectant channels 52 which connect the concentric channel 45 with a needle matching bore 53 formed in the spray tip 51.

The hypodermic needle 7 includes a tapered penetrating tip 54 which communicates with the cannula 8, which cannula 8 terminates in a entrance end 56 which is sized to mate with the bore 53 in the spray tip 51. A perimeter O ring 55 surround the exterior of the entrance end 56 of the needle 7.

Figure 5:
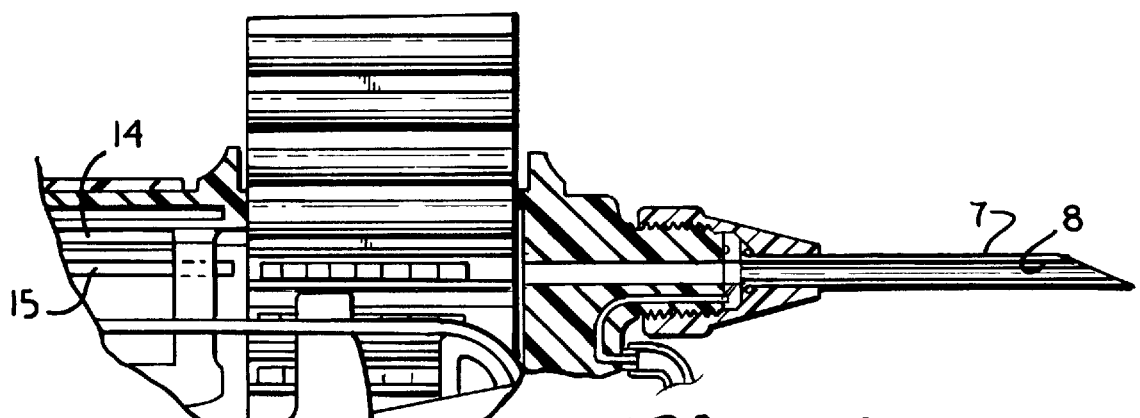
FIG. 5 is a greatly enlarged, fragmentary, cross sectional assembly view, also taken along line 3—3 of FIG. 1, with the needle holder extension threaded onto the implanter to hold the hypodermic needle and spray tip thereon.

In order to attach the needle 7 to the implanter 1, the spray tip 51 is positioned over the needle receiver 33 such that the internal bore 53 in the spray tip 51 is aligned with the internal channel 35 of the needle receiver 33. The needle 7 is then placed onto the spray tip 51 such that the cannula 8 of the needle 7 is aligned with the bore 53 in the spray tip 51. Finally, the needle holder extension 23 is placed over the needle 7 and is threaded onto the needle receiver 33 to clamp the needle 7 and the spray tip 51 in place on the implanter 1 with the O ring 55 sealing the needle cannula 8 to the spray tip internal bore 53, as shown in FIG. 5.

Referring to FIG. 1, in a first embodiment of the invention, a disinfectant reservoir 61 is attached to the exterior of the implanter 1 via a holding strap 62. A tube 63 extends upward from the reservoir 61 to a pump 64 operable by a push button 65. The tube 43 extends from the pump 64 upward to the inlet end 41 (FIG. 3) of the conduit 36. With each operation of the pump 64 accomplished by pushing the push button 65, a quantity of disinfectant is pumped from the reservoir 61 through the tube 63, the pump 64 and the tube 71 to the inlet end 41 of the needle holder conduit 36. The disinfectant then moves through the conduit 36 and into the concentric channel 45 in the spray tip 51 and thence is atomized into a spray as it moves into the spray tip 51 via the channels 52. The sprayed disinfectant thus enters and disinfects 360 degrees about the interior of the cannula 8 of the needle 7. If a quantity of disinfectant is sprayed immediately prior to use of the implanter 1, the disinfectant will be carried into the ear 5 of the animal 6 by the pellet stack 2 as it moves through the needle 7.

Referring to FIG. 2, a second embodiment of the invention is illustrated. As described in the '797 patent, each magazine strip 4 of the implanter 1 has a capacity of twenty pellet doses stored in corresponding pellet chambers 3 which are connected by intervening webs 72. The chambers 3 are slightly conical in shape and are arranged in a side by side parallel relation. The chambers 3 may have internal formations (not shown) to retain the pellets 2 therein. A plurality of strips 4 can be connected in end to end relation to increase the implanting capacity before the implanter 1 requires reloading. A magazine drum 73 can be snapped onto a lower end 74 of the housing grip portion 12. A plurality of end to end connected strips 4 are rolled up into the drum 73 and are fed upwardly through the grip housing portion 8 therefrom. As the pellets 2 in an individual magazine strip 4 are exhausted, the empty strip 4 can be detached from the remaining strips 4 in the implanter 1 and discarded, as taught in the '797 patent.

With the present invention, the magazine drum 73 serves a dual purpose in that a disinfectant reservoir 75 is positioned in the approximate center of the drum 75 such that the pellet strips 4 are wound thereabout in a spiral configuration. A conventional pump (not shown) operated by a push button 81 is positioned within the reservoir 75 such that each operation of the push button 81 sends a quantity of disinfectant upward through an attached tube 82 and into the inlet end 41 of the needle holder conduit 36. The disinfectant is then carried from the conduit 36 and atomized as it enters the needle 7 as described earlier.

A typical quantity of liquid disinfectant pumped with each operation of the push buttons 65 or 81 can be, for example, 0.5 cc. With that quantity dispensed with each dosage of pellets 2, a 1 ounce reservoir 61 or 75 can provide about 100 sprays. These quantities are provided by way of example only, and should not be regarded as limiting in any sense.

It should be noted that the embodiments illustrated and described herein are exemplary only. For example, the reservoir 61 can include a push button sprayer integral therewith instead of separately mounted, as shown in the reservoir 75. Furthermore, the routing of the conduit 36 is simply one of several variations which can be used to accomplish the goal of delivering a quantity of disinfectant to the spray tip 51. Furthermore, the entire disinfectant dispensing system could be positioned within the implanter housing 11, and disinfectant dispensing and spraying could be done automatically with each operation of the triggering assembly 13. The needle 7 and spray tip 51 could be formed as an integral piece to simplify assembly and prevent leakage where they meet.

It is thus to be understood that while certain forms of the present invention have been illustrated and described herein, it is not to be limited to the specific forms or arrangement of parts described and shown.

What is claimed and desired to be secured by letters patent is as follows:

1. In an implanter apparatus for implanting pellet(s) in an animal through a cannula of a hypodermic needle which is connected to the implanter apparatus via a needle holder assembly, the improvement comprising:

a. a liquid reservoir;

b. a conduit having an inlet opening connectable to said reservoir and an exit opening which connects with an interior of the needle cannula; and c. means for selectively dispensing liquid from said reservoir to said conduit independently of the implanting of the pellets.

2. An implanter apparatus as in claim 1, said means for dispensing comprising:

(a) a pump connected between said reservoir and said conduit.

3. An implanter apparatus as in claim 1, the improvement further comprising:

(a) a spray tip provided within said needle holder assembly, said spray tip being positioned to connect said conduit exit end to said cannula interior.

4. An implanter apparatus as in claim 3, wherein said spray tip includes:

(a) an internal bore sized and positioned to mate with said cannula interior;

(b) a concentric channel which is positioned to connect to said conduit exit opening; and (c) one or more conveying channels connecting said concentric channel with said internal bore.

5. An implanter apparatus as set forth in claim 1, including a housing with a grip portion, said implanter injecting a dose of said pellets through said needle cannula via an impeller in response to squeezing of said grip portion, and including:

(a) a pellet magazine having a plurality of pellet doses packaged therein, said magazine extending through said grip to enable said pellet doses to be successively aligned between said impeller and said needle;

(b) a magazine drum attached to a bottom of said grip portion, said magazine drum holding an extension of said pellet magazine in a spiral therein; and (c) said reservoir is positioned in said magazine drum within said spiral.

6. In an implanter apparatus which implants pellet(s) in an animal through a cannula of a hypodermic needle which is connected to the implanter apparatus via a needle holder assembly, the improvement comprising:

a. a liquid reservoir;

b. a conduit having an inlet opening connectable to said reservoir and an exit opening;

c. a pump connected between said reservoir and said conduit which selectively dispenses liquid from said reservoir to said conduit; and d. a spray tip provided within said needle holder assembly, said spray tip being positioned to connect said conduit exit opening directly to the interior of said needle cannula such that disinfectant spray is distributed inside the needle cannula.

7. An implanter apparatus as in claim 6, wherein said spray tip includes:

(a) an internal bore sized and positioned to mate with said cannula in the needle;

(b) a concentric channel which is positioned to connect to said conduit exit opening; and (c) one or more conveying channels connecting said concentric channel with said internal bore.

8. An implanter apparatus as set forth in claim 6, including a housing with a grip portion, said implanter injecting a dose of said pellets through said needle cannula via an impeller in response to squeezing of said grip portion, and including:

(a) a pellet magazine having a plurality of pellet doses packaged therein, said magazine extending through said grip to enable said pellet doses to be successively aligned between said impeller and said needle;

(b) a magazine drum attached to a bottom of said grip portion, said magazine drum holding an extension of said pellet magazine in a spiral therein; and (c) said reservoir is positioned in said magazine drum within said spiral.

9. A method of disinfecting a hypodermic needle of an implanter apparatus which implants pellet(s) in an animal through a cannula of the hypodermic needle, which needle is connected to the implanter apparatus via a needle holder assembly, said method including the steps of:

a. attaching a disinfectant reservoir to the implanter;

b. forming a conduit in said implanter, said conduit having an inlet opening connectable to said reservoir and an exit opening which connects with the interior of said needle cannula;

c. connecting a pump between said reservoir and said conduit inlet opening which selectively dispenses liquid from said reservoir to said conduit; and d. operating said pump independently of the implanting of pellet(s) by the implanter apparatus to dispense a quantity of disinfectant from said reservoir to said needle cannula via said conduit.

10. A method as in claim 9, and further comprising the step of:

(a) providing a spray tip within said needle holder assembly, said spray tip being positioned to connect said conduit exit opening to the interior of said needle cannula.

11. A method as in claim 9, wherein said implanter includes a housing with a grip portion and a trigger assembly, said implanter injecting a stack of said pellets through said needle cannula via an impeller in response to squeezing of said trigger assembly and including a pellet magazine having a plurality of pellet doses packaged therein, said magazine extending through said grip to enable said pellet stacks to be successively aligned between said impeller and said needle and a magazine drum attached to a bottom of said grip portion, said magazine drum holding an extension of said pellet magazine in a spiral configuration therein, said step of attaching a reservoir to said implanter comprising:

(a) positioning said reservoir in the magazine drum within said spiral.

12. In an implanter apparatus for implanting pellet(s) in an animal through a cannula of a hypodermic needle which is connected to the implanter apparatus via a needle holder assembly, the implanter apparatus including a housing with a grip portion, said implanter injecting a dose of said pellets through said needle cannula via an impeller in response to squeezing of said grip portion, the improvement comprising:

a. a liquid reservoir;

b. a conduit having an inlet opening connectable to said reservoir and an exit opening which connects with an interior of the needle cannula;

c. means for selectively dispensing liquid from said reservoir to said conduit;

d. a pellet magazine having a plurality of pellet doses packaged therein, said magazine extending through said grip to enable said pellet doses to be successively aligned between said impeller and said needle;

e. a magazine drum attached to a bottom of said grip portion, said magazine drum holding an extension of said pellet magazine in a spiral therein; and f. said reservoir is positioned in said magazine drum within said spiral.

13. An implanter apparatus as in claim 12, said means for dispensing comprising:

a. a pump connected between said reservoir and said conduit.

14. An implanter apparatus as in claim 12, the improvement further comprising:

a. a spray tip provided within said needle holder assembly, said spray tip being positioned to connect said conduit exit end to said cannula interior.

15. An implanter apparatus as in claim 14, wherein said spray tip includes:

a. an internal bore sized and positioned to mate with said cannula interior;

b. a concentric channel which is positioned to connect to said conduit exit opening; and c. one or more conveying channels connecting said concentric channel with said internal bore.

16. A method of disinfecting a hypodermic needle of an implanter apparatus which implants pellet(s) in an animal through a cannula of the hypodermic needle, which needle is connected to the implanter apparatus via a needle holder assembly, said implanter including a housing with a grip portion and a trigger assembly, said implanter injecting a stack of said pellets through said needle cannula via an impeller in response to squeezing of said trigger assembly and including a pellet magazine having a plurality of pellet doses packaged therein, said magazine extending through said grip to enable said pellet stacks to be successively aligned between said impeller and said needle and a magazine drum attached to a bottom of said grip portion, said magazine drum holding an extension of said pellet magazine in a spiral configuration therein, said method including the steps of:

a. attaching a disinfectant reservoir to the implanter by positioning said reservoir in the magazine drum within said spiral;

b. forming a conduit in said implanter, said conduit having an inlet opening connectable to said reservoir and an exit opening which connects with the interior of said needle cannula;

c. connecting a pump between said reservoir and said conduit inlet opening which selectively dispenses liquid from said reservoir to said conduit; and d. operating said pump to dispense a quantity of disinfectant from said reservoir to said needle cannula via said conduit.

17. A method as in claim 16, and further comprising the step of:

a. providing a spray tip within said needle holder assembly, said spray tip being positioned to connect said conduit exit opening to the interior of said needle cannula.

18. A method as in claim 16, wherein said pump operating step comprises:

a. operating said pump independently of the operation of said trigger assembly.

* * * * *